United States Patent [19]

Takagi et al.

[11] Patent Number: 5,436,158
[45] Date of Patent: Jul. 25, 1995

[54] RHIZOPUS HOST VECTOR SYSTEM

[75] Inventors: Masamichi Takagi, Fuchu; Hiroyuki Horiuchi, Tokyo; Koji Yanai, Urawa; Kenji Sakaguchi, Tokyo, all of Japan

[73] Assignee: Nihon Shokuhin Kako Co., Ltd., Tokyo, Japan

[21] Appl. No.: 165,881

[22] Filed: Dec. 14, 1993

Related U.S. Application Data

[63] Continuation of Ser. No. 985,758, Dec. 4, 1992, abandoned, which is a continuation of Ser. No. 770,330, Oct. 3, 1991, abandoned.

[30] Foreign Application Priority Data

Oct. 4, 1990 [JP] Japan .................................. 2-267357
Mar. 4, 1991 [JP] Japan .................................. 3-062693

[51] Int. Cl.⁶ .......................... C12N 1/15; C12N 15/80
[52] U.S. Cl. .................................. 435/254.9; 435/320.1
[58] Field of Search ................. 435/320.1, 254.9, 69.1

[56] References Cited

FOREIGN PATENT DOCUMENTS

| | | | |
|---|---|---|---|
| 2-53480 | 2/1990 | Japan | C12N 1/15 |
| 8603774 | 7/1986 | WIPO | C12N 15/00 |
| 9000192 | 1/1990 | WIPO | C12N 1/15 |
| 9100920 | 1/1991 | WIPO | C12P 21/02 |

OTHER PUBLICATIONS

Revuelta et al. (Oct. 1986), Proc. Nat. Acad. Sci. USA, vol. 83, pp. 7344–7347.
Yanai et al. (1990), Agric. Biol. Chem., vol. 54(10), pp. 2689–2696. (Biol. Abstr. 91(5):AB-361, Ref. No. 49416).
Sambrook et al., Molecular Cloning: A Laboratory Manual, Second ed., Cold Spring Harbor Laboratory Press, (Cold Spring Harbor, N.Y.), 1989, pp. 17.32–17.44.
Yanai et al. (1991), Curr. Genet. 19:221–226.
Saurez et al. (1988), Mol. Gen. Genet. 212:120–123.
Yanai et al. (1990), Agric. Biol. Chem. 54(10):2689–2696.

*Primary Examiner*—Richard A. Schwartz
*Assistant Examiner*—Philip W. Carter
*Attorney, Agent, or Firm*—Burns, Doane, Swecker & Mathis

[57] ABSTRACT

A host vector system comprising Rhizopus species such as Rhizopus niveus (IFO4810) and a plasmid derived from Phycomycetes such as Mucor, Phycomyces and Absidia wherein the plasmid is contained in a chromosome and/or cytoplasm of the Rhizopus species. The host vector system is suitable for the extracellular production of proteins and enzymes. A process for preparing the host vector system is also provided.

7 Claims, 4 Drawing Sheets

FUGURE 3
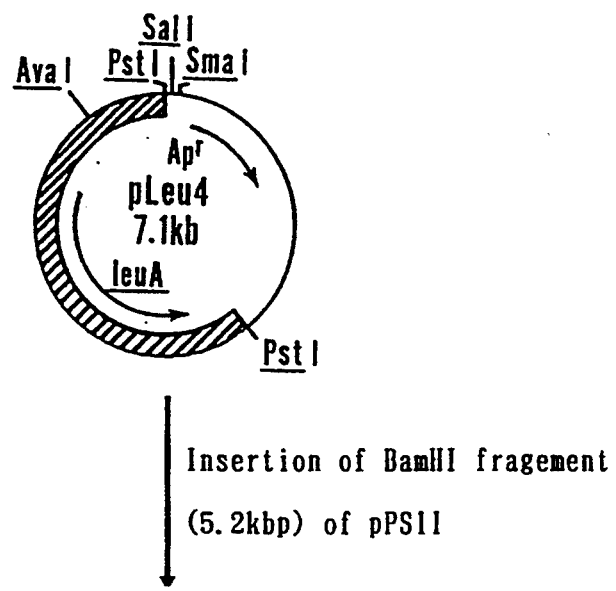
Insertion of BamHI fragement
(5.2kbp) of pPS11
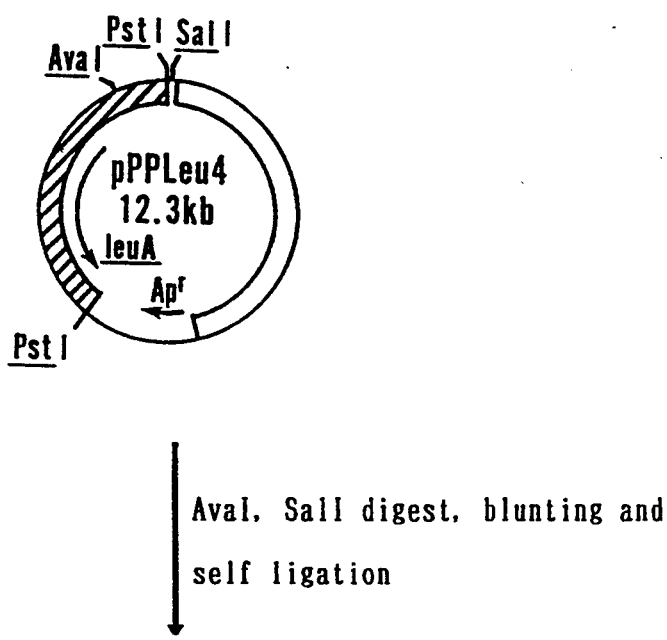
AvaI, SalI digest, blunting and
self ligation
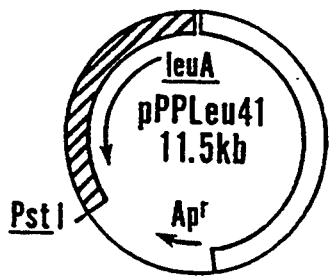

FUGURE 4
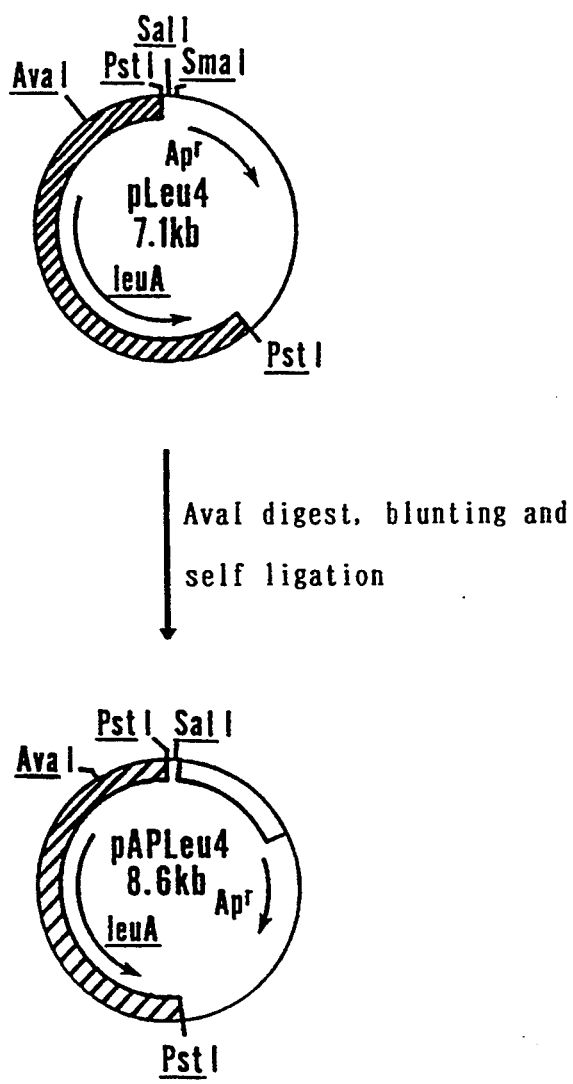

RHIZOPUS HOST VECTOR SYSTEM

This application is a continuation of application Ser. No. 07/985,758, filed Dec. 4, 1992, now abandoned which is a continuation of application Ser. No. 07/770,330, filed Oct. 3, 1991, now abandoned.

BACKGROUND OF THE INVENTION

1. Field of the invention

The present invention relates to a novel host vector system. In particular, the present invention relates to novel host vector system in which hosts are Rhizopus niveus and related molds belonging to phycomycetes, and vectors are also derived from various phycomycetes species.

2. Description of the related art

A method for preparing useful proteins such a interferon, interleukin and others by genetically engineere bacteria has been established. However, problems are no occurring in the method using bacteria as hosts. Of example, the extracellular secretion of the proteins which is sometimes very necessary for the production of large amounts of target proteins is not very efficient in many bacteria Moreover, the intracellularly produced interferon or interleukin produced in *E. coli* has the wrong secondary structures which is different from that of the natural protein. As a result, the artificial protein is recognize. in a human body as an antigen. Thus denaturation an renaturation procedures of the artificial protein are required prior to the pharmaceutical use of the protein.

An, important advantage of a fungal genetic engineering system is its ability to produce glycosylated protein which is impossible with bacterial host vector systems. Many human and animal hormones and other physiologically important proteins are attached with oligosaccharide chains. These glycomoieties are sometimes necessary for the physiological functions of the human hormones as in the case of erthropioetin, and in many cases increase the stability of target proteins against the attack of proteinases in the culture medium, in the injected body fluids, ect.. Each fungi and yeasts produce different structures of glycomoieties, which gives different recognition signals to the human immunological systems and others. Therefore, the construction of various fungal genetic systems are important. The host vector systems using animal and human cells as hosts produce similar or correctly glycosylated proteins, however, their ability to produce of the target proteins are much lower than the fungal system.

Phycomycetes such as Rhizopus or Mucor are used frequently in fermentation technology. They are classified into Phycomycetes. Rhizopus has the extensive ability to secrete enzymes and proteins extracellularly For instance, the amount of glucoamylase secreted by *Rhizopus niveus* into the liquid culture medium is about 2 g/liter and that secreted with solid culture procedure it about 30 g/kg. Further, not only the primary structure but the secondary structure of the resulting protein is the same as that of a natural protein due to the extracellular secretion system through membrane. Therefore, it is expected that transformed molds will be used for the preparation of various kinds of commercially important enzymes and proteins. However, only a few transformation techniques are established for fungi and no transformation techniques for Rhizopus known. Under the circumstances, the present inventors successfully provided a transformation technique used for Rhizopus(see Japanese Patent Disclosure (KOKAI) (JP-A-) 2-53480). However, a vector suitable for producing an enzyme by using Rhizopus as a host has not been known.

An object of the present invention is to provide a host vector system suitable for the production of proteins and enzymes using. Rhizopus as a host Rhizopus has the enhanced ability to produce proteins and enzymes extracellularly and in the cell because of their large cell mass production

SUMMARY OF THE INVENTION

The present invention relates to a host vector system comprising Rhizopus species and a plasmid derived from various Phycomycetes wherein the plasmid is contained in chromosome and/or cytoplasm of the Rhizopus species.

BRIEF DESCRIPTION OF THE DRAWINGS

FIGS. 2 and 3 illustrate a preparation method for plasmids pJPLeu4 and pJPLeu41. FIG. 4 illustrates a preparation method for plasmid pJPLeu41.

DETAILED DESCRIPTION OF THE INVENTION

Figure 1:
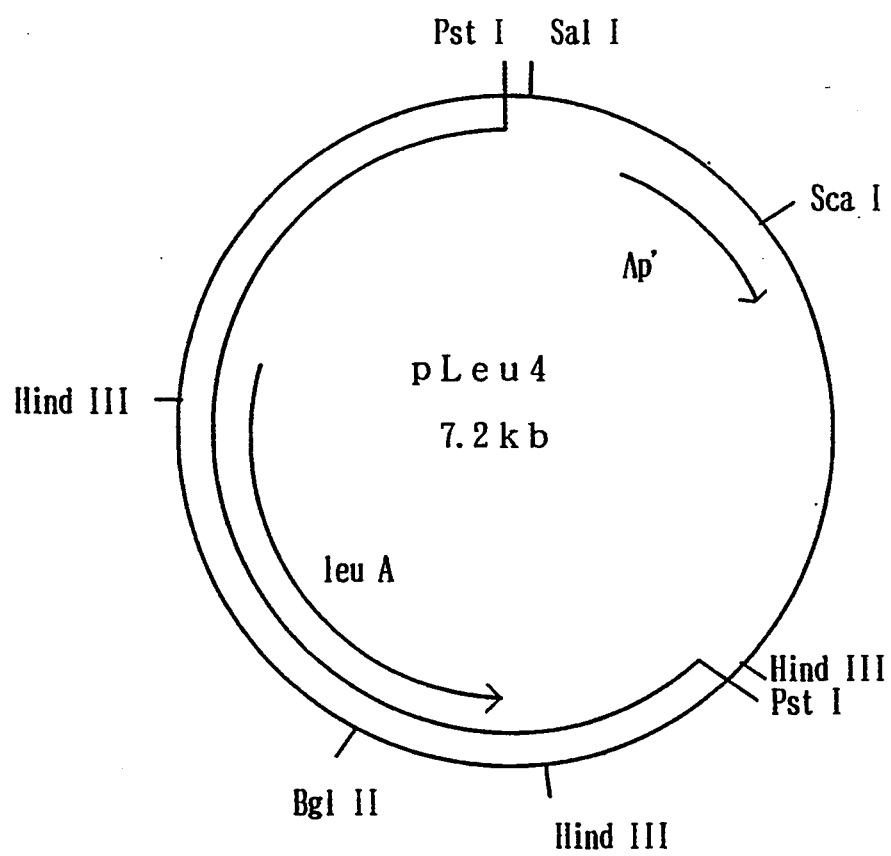
FIG. 1 illustrates a restriction map of plasmid pLneu4.

Filamentous fungi *Rhizopus niveus* (IFO4810) is used as a host of the host vector system of the invention. Further, Rhizopus species can be selected from the group consisting of *Rhizopus delemar* such as ATCC 9374 strain, *Rhizopus javanicus* such as ATCC 22581 and 22580 strains, *Rhizopus oligosporus* such as ATCC 22959 strain, *Rhizopus nigricans* such as ATCC 24862 strain and *Rhizopus oryzae* such as JCM 5557=IAM 6015 and JCM 5558=IAM 6019 strains.

A plasmid derived from phycomycetes is a vector of the system of the invention. The use of the plasmid derived from phycomycetes as the vector enables the transformation of the host, *Rhizopus niveus*. Examples of phycomycetes include Mucor such as *Mucor circinelloides* and *Mucor javanicus* Phycomyces such as *Phycomyces blakesleeanus* and *Phycomyce nitens*; Absidia such as *Absidia glauca Absidia coerule* and *Absidia megaspora.*

Examples of the plasmid derived from phycomycete include plasmids pLeu4, pPSll, pMA67, pJL1, pJL2, pMCL1302 pMCL002, pJPLeu4, pPPLeu4, pLeu41, pJPLeu41 and pPPLeu41

The above-mentioned plasmids are obtainable according to the following methods.

Plasmid pLeu4 is obtainable in accordance with the method reported in the article by Roncero, M.I.G. et al Gene, 84, 335-343 (1989). The disclosure of which hereby incorporated by reference.

Plasmid pPSll is obtainable from *Phycomyces blakeseeanus* (NRRL1555 strain) according to the method reported in the article by T. Suarez et al, Mol. Gen. Gene 212, 120-123, 1988. The disclosure of which is hereby incorporated by reference.

Plasmid pMA67 is obtainable from plasmid pMCL130 according to the method reported in the article by L. Dickinson et al, Carsberg Research Communications, 52, 243-252, 1987. The disclosure of which is hereby incorporated by reference.

Plasmids pJL1 and pJL2 are obtainable from *Phycomyces blakesleeanus* (A459 strain) according to the method reported in the article by J. L. Revuetta et al, Proc. Nat. Acad. Sci. U.S.A., 83, 7344-7347, 1986. The disclosure of which is hereby incorporated by reference. Plasmids pMCL1302 and pMCL002 are obtainable from *Mucor circinelloides* f. *lusitanicus* (CBS227.49 strain) which is the same as *Mucor racemosus* (ATCC 12166 strain) according to the method reported in the article by R. van Heeswijck, Carsberg Research Communications, 51, 433–443, 1986. The disclosure of which is hereby incorporated by reference. Plasmid pJPLeu4 is obtainable by insertion of an EcoRI-XbaI fragment (0.9 kbp) of plasmid pJL2 into a SamI site of pLeu4. pJPLeu41 is obtainable by digestion of plasmid pJPLeu4 with restriction enzymes AvaI and SalI, and self ligation of the fragment of 7.2 kbp obtained by the digestion. Plasmid pPPLeu4 is obtainable by insertion of a BamHI fragment (5.2 kbp) obtained from plasmid pPSll into a SamI site of pLeu4. Plasmid pPPLeu41 is obtainable by digestion of plasmid pPPLeu4 with restriction enzymes AvaI and SalI, and self ligation of the fragment of 11.5 kbp obtained by the digestion. Plasmid pLeu41 is obtainable by digestion of plasmid pLeu4 with restriction enzymes AvaI and SalI, and self ligation of the fragment of 6.3 kbp obtained by the digestion.

The abovementioned vector(s) is inserted into chromosome(s) of a host(s) *Rhizopus niveus*, or contained in a cytoplasm(s) of *Rhizopus niveus*. Further it is possible that the vector(s) is inserted into a chromosome(s) of *Rhizopus niveus* and contained in a cytoplasm(s) of *Rhizopus niveus* simultaneously. When the vector(s) is inserted into the chromosome(s) of *Rhizopus niveus*, the number of the vector(s) inserted into a chromosome is one or more. When the vector(s) is contained in the cytoplasm(s) of *Rhizopus niveus*, the number of the vector(s) contained in a cytoplasm of is also one or more. The host vector system of the present invention can be prepared based on the method mentioned in Japanese Patent Disclosure (KOKAI) (JP-A-) 2-53480. The disclosure of which is hereby incorporated by reference.

Spores of *Rhizopus niveus* are cultured to obtain germination tubes. The germination tubes, spores or mycelia are treated with Novozym 234, chitinase and chitosanase to obtain protoplast cells. The cells are treated with polyethylene glycol in the presence of plasmids of Phycomycetes to obtain fused cells containing the plasmids of Phycomycetes. The host vector system of the present invention is obtained by subjecting the fused cells to renaturation.

The plasmids of Phycomycetes are usually cyclic and the cyclic one can be, used as they are. Alternatively, the plasmids are in a linear DNA(s) form which are obtained by cutting the plasmid with a suitable restriction enzyme(s) There is a tendency that the rate of transformation is high when the cyclic plasmids are used and that the insertion rate of the plasmid(s) into a chromosome is high when the linear one is used.

EXAMPLES

The present invention is illustrated more in detail in reference to the following examples.

EXAMPLE 1

Preparation of auxotrophic mutant 1 ml of a suspension solution containing $10^{6.6}$-$10^{7.7}$ pieces/ml of spores of *Rhizopus niveus* was irradiated with UV ray (0.0036 J/cm$^2$) and the viability was measured. The solution was applied on a plate complete agar medium. After culturing at 37° for about 20 days, spores were collected and washed with a saline solution. Then the resulting spores were subjected to stationary culture in a liquid minimal medium at 30° and filtered with a G3 glass filter. These procedures were repeated until the spores no longer grew.

The spores which were obtained were suspended in a saline solution, and the suspension was applied on an acid complete agar medium plate (2.4% potato dextrose (available from Difco), 0.1% HCl, 1.5% agar) and cultured at 30° for 2-3 day . After culturing, the spores on the medium were replicated onto a minimal agar medium (2% glucose, 0.2% asparagine, 0.05% $KH_2PO_4$, 0.025% $MgSO_4$, .7$H_2O$, 1.5% purified agar) containing various amino acids and nucleic acids.

A leucine (leu) auxotrophic mutant was selected from the replicated spores by a general method to obtain *R. niveus* M 37 strain.

Transformation of *Rhizopus niveus*

$2-5 \times 10^{7.7}$ pieces of the resulting *R. niveus* M 37 strain, a leu auxotrophic mutant, were suspended in water and filtered with a G1 glass filter. The resultant filtrate was filtered with a G3 glass filter. The filtrate which was obtained was centrifuged at 2500 rpm for 7 minutes. The precipitate was suspended in 5-8 ml of a solution containing 1% glucose, 20% yeast extract, 2% polypeptone and 0.01M proline and subjected to a shaking culture with a reciprocal shaker at 300 rpm at 30 for 4.5 to 5 hours After the formation of germination tubes was confirmed by the observation with a microscope, the suspension was filtered with a G1 glass filter and the filtrate was centrifuged at 3000 rpm for 3 minutes. The precipitate was suspended in 5 ml of buffer solution (A) (13.2 mM citric acid, 33 mM $Na_2HPO_4$, 0.3M mannitol) and centrifuged at 3000 rpm for 3 minutes. The precipitate was suspended in buffer solution (A) again and centrifuged at 3000 rpm for 3 minutes.

The resulting precipitate was suspended in 2 ml of buffer solution (A). 35 mg of Novozym 234 (available from Novo corporation, in Denmark), 14 mg of chitinase ABC (available from Advanced Biofactures) and 10 units of chitosanase (available from Wako in Japan) were suspended in 5 ml of buffer solution (A). The suspension was added to the precipitate suspension and subjected to a shaking culture by the use of a reciprocal shaker (at 60 rpm) at 30° for 1.5 to 2 hours. After the formation of protoplast cells was confirmed by observation with a microscope, the suspension was filtered with a G2 glass filter. The filtrate was centrifuged at 450 rpm for 4 minutes. The precipitate was suspended in 5 ml of buffer solution (B) (10 mM MOPS (pH 6.3), 50 mM $CaCl_2$, 0.3M mannitol) and centrifuged at 450 rpm for 4 minutes. These suspension and centrifugation procedures were repeated twice. The precipitate was suspended gradually in 200 μl of buffer solution (B), and mixed with 10 μl of a plasmid pLeu4 (Roncero, M.I.G. et al, Gene, 84, 335-343(1989; plasmid pLeu4 has a leuA gene of *Mucor circienelloides* and an ARS element working in *Mucor circienelloides*) suspension prepared by suspending about 10 to 20μg of pLeu4 in 10μl of a solution containing 10 mM MOPS (pH 6.3), 50 mM $CaCl_2$ and 1 mg/20μlG, 1 of heparin. The mixture was allowed to stand for 5 minutes in an ice bath and 10μl of buffer solution (C) (10 mM MOPS (pH 6.3), 50 mM $CaCl_2$, 40% PEG 4000 solution) was added. The mixture was allowed to stand for 25 minutes in an ice bath and 1.25 ml of buffer solution (C) was further added. Then the mixture was allowed to stand for 25 minutes at room temperature. The mixture was mixed with 10 ml of buffer solution (B) and centrifuged at 600 rpm for 3 minutes.

The precipitate was suspended in 1 ml of a solution containing 1% glucose, 2% yeast extract, 2% polypeptone and 0.3M mannitol. The suspension was transferred to an Eppendrof tube and subjected to the stationary culture at 30° C. for 30 minutes. Then the suspension was centrifuged at 1000 rpm for 1 minute. The precipitate was suspended in 1 ml of 0.4M mannitol solution and centrifuged at 1000 rpm for 1 minute. These suspension and centrifugation procedures were repeated twice. The precipitate was suspended in 100 $\mu$l of 0.4M mannitol solution and mixed with 5 ml of medium (D) (SIV minimal medium, 0.35M mannitol .and 0.2% $H_2SO_4$ were dissolved at 48° C. ) containing 1% purified agar. Then the mixture was placed on a plate medium (D) containing 1.5% purified agar to form a layer and cultured at 30° C. for to 3 days. Each colony was replicated to SIV minimal medium and stored. That is, plasmid pLeu4 was complementary to R. niveus M 37 strain being leu auxotroph and it was clarified that plasmid pLeu4 was functionable in R. niveus M 37 strain as a vector.

| SIV minimal medium | |
|---|---|
| Solution (A): | |
| Distilled water | 480 ml |
| Nitrogen source, Asparagine | 2 g |
| 50 times concentrated solution (%) | 20 ml |
| Powder agar | 15 g |
| Solution (B): | |
| Distilled water | 490 ml |
| Glucose | 20 g |

Solution (A) and solution (B) were treated in an autoclave respectively and mixed.

| (*) 50 times concentrated solution: | |
|---|---|
| $KH_2PO_4$ | 250 g |
| $MgSO_4.7H_2O$ | 25 g |
| Trace elements | 5 ml |
| 14% (w/w) $CaCl_2$ solution | 10 ml |
| Thiamine.HCl | 100 mg |
| Distilled water | 1000 ml |

| (**) Trace elements: | |
|---|---|
| Citric acid.$H_2O$ | 2 g |
| $Fe(NO_3)_2.9H_2O$ | 1.5 g |
| $ZnSO_4.7H_2O$ | 1 g |
| $MnSO_4.H_2O$ | 300 mg |
| $CuSO_4.5H_2O$ | 50 mg |
| $NaMoO_4.2H_2O$ | 50 mg |

All DNAs were extracted from the obtained transformants and subjected to an analysis by southern blot technique As a result, plasmid pLeu4 was inserted into a chromosom of Rhizopus niveus M 37 strain in the form of tandem or contained in a cytoplasm of Rhizopus niveus M 37 strain E. coli was transformed by using all DNAs extracted from the obtained transformants. Then the plasmid pLeu4 was recovered in its complete form from the transformed E. coli cells. This means that plasmid pLeu4 contained the ARS activity and was replicable in Rhizopus niveus M 3 strain.

EXAMPLE 2

With the same procedures described in Example 1, the linear DNA fragments obtained by cutting the cyclic plasmid pLeu4 with each one of 4 kinds of restriction enzymes (Pst I, Bgl II , Sac I and Sca I ) were transformed into Rhizopus niveus. The cyclic plasmid pLeu4 was the same as that use in Example 1 and of which restriction map is shown 1 FIG. 1 . As a result, leu auxotrophy was compensated by use of every fragment. All DNAs of the obtained transformants were subjected to an analysis by southern blot technique. As a result, ratio of plasmids inserted into chromosomes was higher than that of the transformation using cyclic plasmids.

EXAMPLE 3

Rhizopus niveus was plated on a PD medium or minimal medium and cultured at 30° C. for about 10 days to obtain spores. Conidiophores were collected from each mycelium and suspended in 30 ml of sterilized water. Then the water was stirred strongly to release spores included in the conidiophores. The spores were collected by a G3 glass filter from the resulting suspension. The spore suspension was centrifuged at 3000 rpm at room temperature for 1 minutes to collect spores. The spores were washed with a. saline and suspended ($2-5 \times 10^7$ pieces/ml) in a YPG liquid medium , (1% glucose, 2% polypeptone, 2% yeast extract). The spore suspension was poured into a sterilized test tube with a cotton plug and subjected to a shaking culture at 30 ° C. for about 5 hours (a reciprocal shaker at 300 rpm) until germination tubes were formed. Then spores excessively germinated were removed from spores immediately after germination. The filtrate was centrifuged and the precipitate was washed with 0.3 x McIlvaine buffer solution (13.3 mM citric acid, 33 mM $Na_2HPO_4$, pH 5.6) twice to substitute the buffer solution.

The germinated spores were suspended in 7 ml of above mentioned buffer solution containing 5 mg/ml of Novozym 234 (available from Novo corporation in Denmark), 2 mg/ml of chitinase ABC (available from Advanced Biofactures and 1.52 mg/ml of chitosanase (available from Wako in Japan). The resulting suspension was added to a plastic tube and subjected to a shaking culture at 40 rpm at 30° for 1.5 to 2 hours. The residue of protoplasted cells was removed and the filtrate was subjected to centrifugation by a swing rotor (70$\times$g) for 4 minutes collect protoplast cells. The collected cells were washed with buffer solution (A) twice and suspended in 400$\mu$l of buffer solution (A) (10 mM MOPS (pH 6.3), 50 mM $CaCl_2$,0.3 M mannitol). 100$\mu$l of the resulting solution was mixed with a plasmid DNA solution which was prepared in advance by dissolving plasmid pLeu4 in 10$\mu$l of buffer solution (C) (buffer solution (A) added with hepaline in the concentration of 50 mg/ml) and being allowed to stand in an ice bath for 20 minutes or more. The mixture was allowed to stand in an ice bath for 5 minutes, and 10$\mu$l of 40% PF solution (10 mM MOPS (pH 6.3), 50 mM $CaCl_2$, 40% PEG 4000 solution) was added. The mixture was mixed slowly and allowed to stand for 25 minutes in an ice bath.

1.25, ml of the 40% PEG solution was further added. Then the mixture was allowed to stand for 25 minutes at room temperature. The mixture was mixed with 10 ml of buffer solution (A) and was subjected to centrifugation by a swing rotor (50$\times$g) for 4 minutes to collect cells. 1 ml of YPG medium containing 0.3M mannitol was added to the collected protoplast cells and allowed to stand at 30° for 30 minutes. Then the protoplast cells were washed 0.4M mannitol solution twice and plated on a minimal medium. The number of generated colonies was counted and the colony number per 1μg of DNA used was calculated. The result were listed in Tables 1 and 2.

TABLE 1

| Plasmid | transformation frequency (cfu/μg) | | |
|---|---|---|---|
| | ex 1 | ex 2 | ex 3 |
| pLeu4 | 0.56 (1) | 2.1 (1) | 0.2 (1) |
| pJLeu4 | 1.52 (2.71) | 6.85 (3.26) | 0.6 (3) |
| pPPLeu4 | 10.4 (1.85) | 7.7 (3.66) | 1.3 (6.5) |

In ex 1, ex 2 and ex 3, 25, 20 and 10μg of plasmid DNA was used respectively.

TABLE 2

| Plasmid | transformation frequency (cfu/μg) | | |
|---|---|---|---|
| | ex 1 | ex 2 | ex 3 |
| pLeu4 | 2.2 (1) | 1.5 (1) | 3.6 (1) |
| pLeu41 | 3.95 (1.79) | 2.0 (1.33) | 4.8 (1.33) |
| pJPLeu41 | 8.55 (3.88) | 4.6 (3.07) | 7.1 (1.97) |
| pPPLeu41 | 6.7 (3.04) | 3.1 (2.07) | N.T. |

In ex 1, ex 2 and ex 3, 25, 20 and 10g of plasmid DNA was respectively used.

N.T.: not tested

Figure 2:
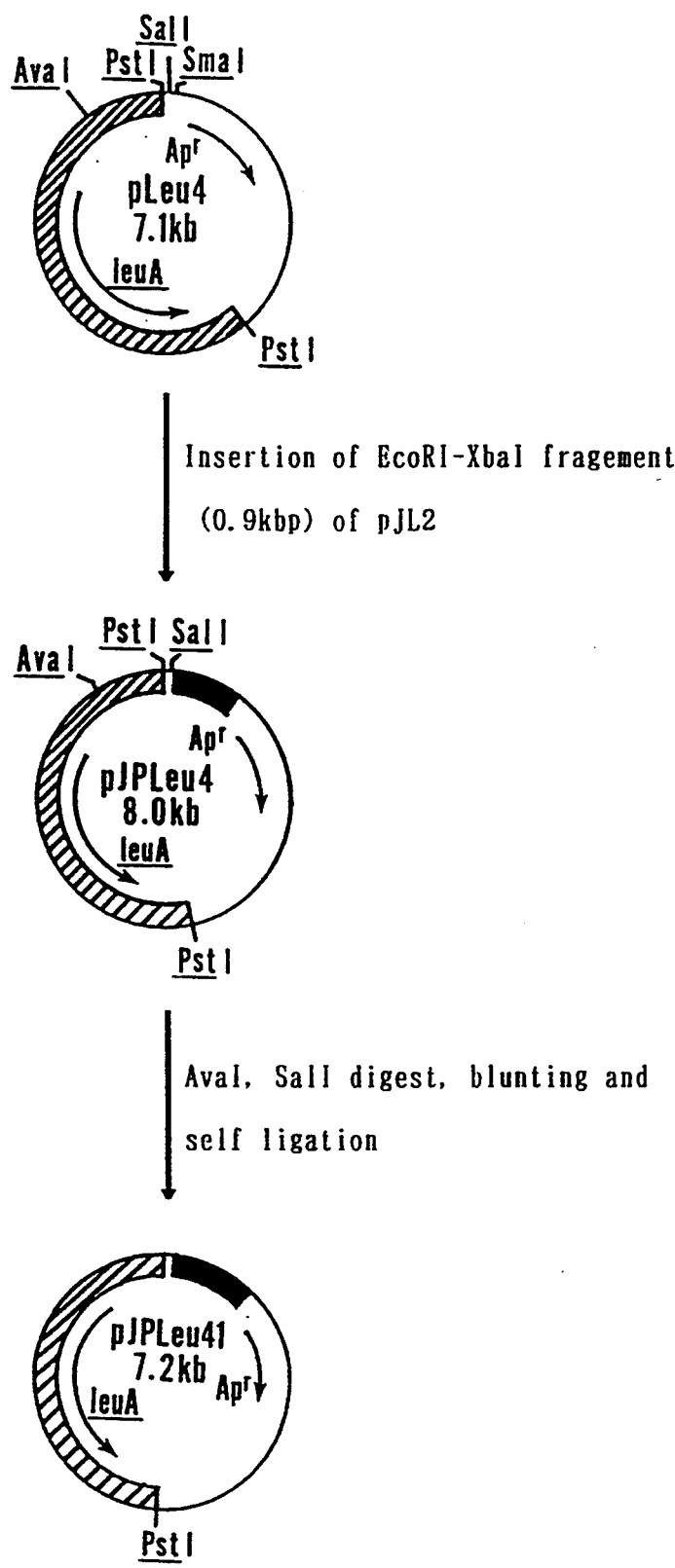

Plasmid DNA used in the above experiments was prepare in accordance with the flow charts shown in FIGS. 2 to 4 as explained below. pJPLeu4: An EcoRI-XbaI fragment (0.9 kbp) was isolate from plasmid pJL2 and the termini of the fragment was made smooth with T4 polymerase. The fragment was ligated by using T4 DNA ligase to plasmid pLeu4 which was previously digested with Sam I and dephosphorylated to obtain plasmid pJPLeu4.

pJPLeu41: Plasmid pJPLeu41 was obtained by digesting plasmid pJPLeu4 with Ava I and Sal I, blunting the termini of the resulting 7.2 kbp fragment with T4 polymerase and self ligating the fragment. pPPLeu4: BamHI fragment (5.2 kbp) was isolated from plasmid pPSll and the termini of the resulting 7.2 kb fragment was made smooth with T4 polymerase. The fragment was ligated by using T4 DNA ligase to plasmid pLeu4 which was previously digested with Sam I and dephosphorylated to obtain plasmid pJPLeu4.

pPPLeu41: Plasmid pPPLeu41 was obtained by digesting pPPLeu4 with AvaI and SalI, blunting the termini of the resulting 11.5 kbp fragment with T4 polymerase and self ligating the fragment.

pLeu41: Plasmid pLeu41 was obtained by digesting pLeu4 with AvaI and SalI, blunting the termini of the resulting 6.3 kbp fragment with T4 polymerase and self ligating the fragment.

What we claim is:

1. A host vector system for the production of a target protein in Rhizopus said system comprising a Rhizopus species transformed with at least one plasmid derived from *Mucor circinelloides* wherein said plasmid contains an origin of replication from pLeu4 and encodes said target protein.

2. The host vector system of claim 1, wherein the Rhizopus species is selected from the group consisting of *Rhizopus niveus, Rhizopus delemar, Rhizopus javanicus, Rhizopus oligosporus, Rhizopus nigricans* and *Rhizopus oryzae*.

3. The host vector system of claim 2 wherein the Rhizopus species is *Rhizopus niveus*.

4. The host vector system of claim 3 wherein at least one plasmid is integrated into a chromosome of *Rhizopus niveus*.

5. The host vector system of claim 3 wherein at least one plasmid is extrachromosomal.

6. The host vector system of claim 3 wherein at least one plasmid is integrated into a chromosome of *Rhizopus niveus* and at least one plasmid is extrachromosomal.

7. The host vector system of claim 3 wherein the plasmid is pMCL1302, pMCL002, pMA67, pLeu4 or pLeu41.

* * * * *